United States Patent [19]
Hosokoshi et al.

[11] 3,993,487
[45] Nov. 23, 1976

[54] METHOD FOR MANUFACTURE OF COLOR TELEVISION PICTURE TUBES USING ROTATING LIGHT SOURCE

[75] Inventors: Kakuichiro Hosokoshi, Neyagawa; Shigeya Ashizaki, Takatsuki, both of Japan

[73] Assignee: Matsushita Electronics Corporation, Osaka, Japan

[22] Filed: Feb. 18, 1975

[21] Appl. No.: 550,631

[30] Foreign Application Priority Data
Feb. 18, 1974  Japan .............................. 49-19723

[52] U.S. Cl. .................................. 96/36.1; 354/1; 427/68
[51] Int. Cl.² ........................................ G03C 5/00
[58] Field of Search ............... 96/36.1, 27 E; 354/1; 427/68

[56]  References Cited
UNITED STATES PATENTS

| 3,559,546 | 2/1971 | McKee .................................. 354/1 |
| 3,667,947 | 6/1972 | McKee .................................. 96/36.1 |
| 3,725,106 | 4/1973 | Hosokosni ........................... 96/36.1 |
| 3,736,848 | 6/1973 | Tsuneta et al. ....................... 354/1 |
| 3,764,366 | 10/1973 | Ninagawa et al. .................... 96/36.1 |
| 3,779,760 | 12/1973 | Miyaoka .............................. 96/36.1 |
| 3,856,525 | 12/1974 | Inoue ................................. 354/1 X |
| 3,876,425 | 4/1975 | Geenen ............................... 96/36.1 |
| 3,890,151 | 6/1975 | Suzuki et al. ........................ 96/36.1 |
| 3,936,302 | 2/1976 | Takami et al. ....................... 96/36.1 |

*Primary Examiner*—Edward C. Kimlin
*Attorney, Agent, or Firm*—Stevens, Davis, Miller & Mosher

[57]  ABSTRACT

The invention discloses a method and apparatus for manufacture of color television picture tubes of the type having a shadow mask with a multiplicity of slots, and more particularly for selectively exposing a light sensitive film uniformly coated over the inner surface of a face-panel in order to form the temporary dots or strips. The exposure light source is rotated in the form of a ring while it is displaced relative to the light sensitive film in the longitudinal direction of the slots in a shadow mask, whereby the spacing in the longitudinal direction between the adjacent exposed areas or light images projected may be advantageously reduced without reducing the spacing in the longitudinal direction between the adjacent slots in the shadow mask; that is, the width of the bridge therebetween, so that the color television picture tubes with excellent brightness and contrast characteristics may be provided without adversely affecting the mechanical strength of the shadow mask.

3 Claims, 12 Drawing Figures

POSITION

METHOD FOR MANUFACTURE OF COLOR TELEVISION PICTURE TUBES USING ROTATING LIGHT SOURCE

The present invention relates to a method and apparatus for the manufacture of color television picture tubes, more particularly the so-called slot mask-type color television tube wherein a shadow mask with slot-shaped apertures is interposed between the inline type three electron guns and the black matrix type screen and the predetermined phosphor strips surrounded by the light absorbing film on the screen may be excited to luminesce by three electron beams which pass through the slots in the shadow mask.

A method for producing a color television picture tube including a black matrix type screen; that is, a color television picture tube which include a light absorbing matrix as a part of the luminescent screen structure has been described previously; for example in U.S. Pat. No. 3,558,310. According to this patent, the diameter of the phosphor dots on the screen is selected to be less than the diameter of the apertures of the shadow mask, and the phosphor dots are surrounded by the graphite light absorbing film. The light absorbing matrix having a multiplicity of holes therein is formed on the inner surface of the faceplate before the phosphor dots are deposited. Prior to formation of the holes, temporary dots with diameters smaller than that of the apertures are formed.

A method for forming the temporary dots has been described previously; for example, in U.S. Pat. No. 3,725,106. According to this patent, a light sensitive film 2, whose major component is polyvinyl alcohol (PVA), is uniformly coated over the inner surface of a face-panel 1 made of glass as shown in FIG. 1. Thereafter, the light sensitive film 2 is selectively exposed by the ultraviolet rays 8 emitted from a light emitting point of a lamp house 3 including an ultra-high-voltage mercury vapor lamp or the like 3' which form a secondary light source 4. The light from source 4 passes through a correction lens 5 and an aperture 7 of a shadow mask 6 to reach film 2. During the exposure, the light emitting point or secondary light source 4 is caused to revolve in a small circle about its eccentric shaft 9. Therefore, as shown in FIG. 2, the light energy received by the dot-shaped exposed area is greater at the circular center area A, but is less at the annular peripheral area B where the light beam is partially shadowed.

By the exposure, portions of the film where phosphor dots in any one of three colors, i.e., green, red and blue, are to be located are hardened. The lamp house 3 is angularly displaced by 120° in both directions so that the light sensitive film is subjected to the exposure twice in a manner substantially similar to that described above. Therefore, further portions of the film where the remaining two color phosphor dots are to be located are hardened.

Thereafter, the light sensitive film is subjected to the developing process so that the light sensitive film, except the areas A, may be removed. Thus, a number of dot-shaped films or temporary dots which are substantially three times the number of apertures in the shadow mask 6 are formed over the inner surface of the face-panel 1. The diameter of each temporary dot is smaller than that of the corresponding aperture of the shadow mask 6.

Next, a light absorbing film consisting of, for instance, graphite or the like is uniformly coated over the inner surface of the face-panel 1 and is then dried. Thereafter, the temporary dots are dissolved and removed in a suitable manner so that the matrixshaped light absorbing film may be formed upon the inner surface of the face-panel 1. Thereafter, three kinds of color dots are deposited upon the dot-shaped areas previously occupied by the temporary dots.

In the above method, the shadow mask 6 has been described as having a multiplicity of circular apertures, but it may be of the type having a multiplicity of elongated slots.

Referring to FIG. 3, a shadow mask 16 is shown as having a multiplicity of elongated slots 17, and one set of temporary dots 18, 18' and 18'' are shown as being formed upon the inner surface of the face-panel 1.

Both the major and minor diameters of the temporary dots 18, 18' and 18'' are reduced in the same ratio as compared with those of the slots 17 so that the spacing $a$ between the adjacent temporary dots in the longitudinal direction thereof tends to become longer. The spacing $a$ is dependent upon the spacing $b$ in the vertical direction between the adjacent slots 17 of the shadow mask, the spacing $b$ serving as the reinforcing bridge between the adjacent slots. When the spacing $a$ is longer, the effective area of the temporary dot or color strip to be deposited thereupon after the temporary dot is removed becomes so small that the brightness characteristic of the color television tube is adversely affected. On the other hand, if the spacing $a$ is too short, the area occupied by the light absorbing film is reduced so that the contrast characteristic is adversely affected.

In the slot mask type color television tubes, the three electron guns are arrayed in one line in the horizontal direction. Therefore, the temporary dots 18, 18' and 18'' in one set are formed at the areas where the green, blue and red phosphor strips are to be deposited, and the phosphor strips in the same column have the same color. Therefore, even when the spacing $a$ is minimum, color contamination may be avoided, but when the spacing $c$ between the adjacent columns of the color phosphor strips is not sufficient to provide a satisfactory guard band, color purity is adversely affected.

In view of the above, one of the objects of the present invention is to provide a method and apparatus for reducing only the spacing in the longitudinal direction between the phosphor strips; that is, the spacing $a$ in the longitudinal direction between the temporary dots while the spacing $b$ in the longitudinal direction between the slots in the mask, which serves as the reinforcing bridge of the mask, remains longer in the usual manner. According to the present invention, color television tubes with excellent brightness and contrast characteristics may be provided without adversely affecting the mechanical strength of the shadow mask.

According to the present invention, during the selective exposure of the light sensitive film, the light emitting point of the lamp house is rotated in a plane substantially parallel with the light sensitive film, and the relative position between the ring-shaped secondary light source produced by the rotation of the light emitting point and the light sensitive film is displaced in the longitudinal direction of the slot in the mask as will be described in detail hereinafter.

Figure 1:
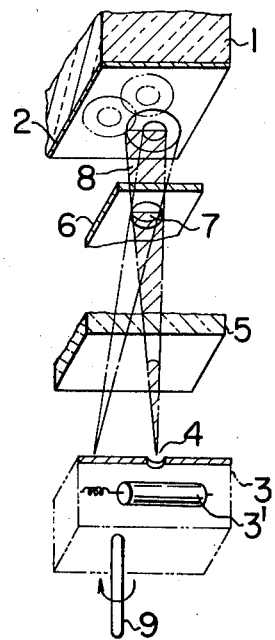
FIG. 1 is a diagram illustrating the light house used for exposing so as to produce the screen of a color television picture tube.
Figure 2:
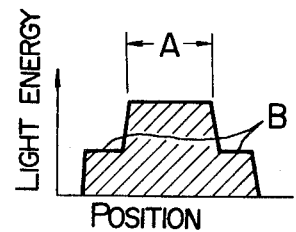
FIG. 2 is a diagram illustrating the light energy distribution in an area exposed by the light house shown in FIG. 1.
Figure 3:
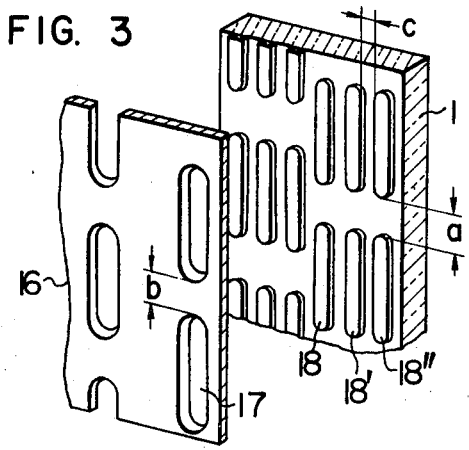
FIG. 3 shows the temporary dots formed by the use of the light house shown in FIG. 1 and the relationship between the temporary dots and a shadow mask with strip-shaped apertures.
Figure 4:
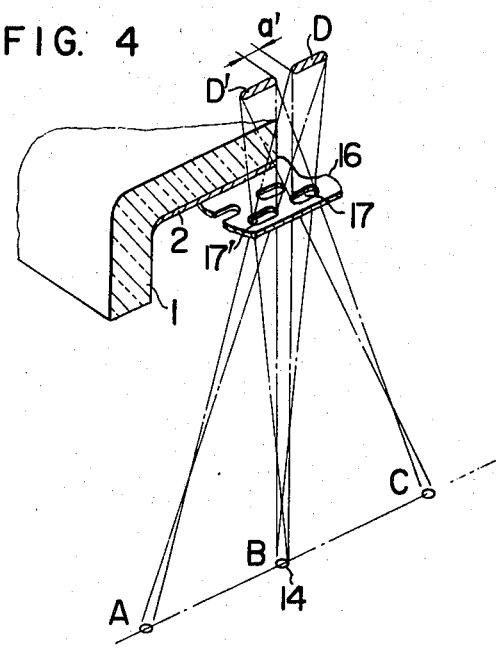
FIG. 4 is a schematic view used for explanation of one preferred embodiment of the present invention.

Referring to FIG. 4, the secondary light source 14 is continuously or intermittently displaced from the point A via the point B to the point C. Alternatively, the light sensitive film coated upon the face-panel and the shadow mask are continuously or intermittently displaced in the longitudinal direction of the slot relative to the secondary light source 14. Therefore, the pattern of the light projected upon the light sensitive film 2 through the shadow mask 16 with slot shaped apertures may be elongated in such a way that the minor diameter of the temporary dot may be made smaller than that of the slot while the major diameter of the temporary dot may be made substantially equal to or slightly longer than that of the slot.

The elongated hatched patterns D and D' are projected when the secondary light source 14 is stopped at the point B, and the spacing therebetween $a'$ is relatively longer. According to the present invention, not only the secondary light source 14 is stopped at the point B, but also it is continuously or intermittently displaced from the point A via the point B to the point C. The point A is so selected that the light beam emitted from the secondary light source 14 at the point A is projected through the slot 17' to form the pattern which may be substantially registered with the pattern D formed on the light sensitive film 2 by the light beam projected through the slot 17 from the secondary light source 14 at the point B. In like manner, the point C is so selected that the light beam emitted from the secondary light source at the point C is projected through the slot 17 to form the pattern D' which may be substantially registered with the pattern formed by the light beam projected through the slot 17' from the secondary light source 14 at the point B.

Figure 5:
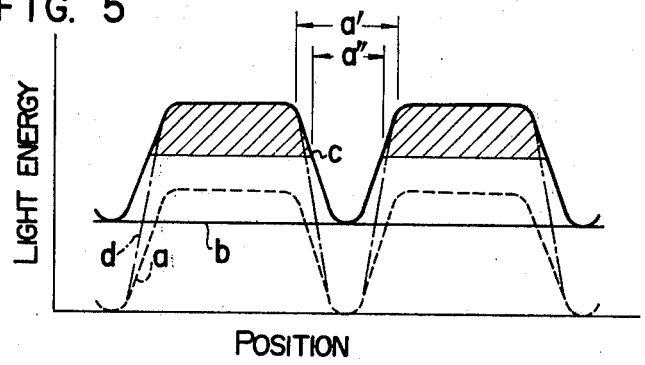
FIG. 5 is a diagram illustrating the light energy received in an area exposed by the apparatus shown in FIG. 4.
Figure 6:
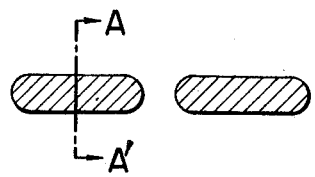
FIG. 6 is a top view thereof.
Figure 7:
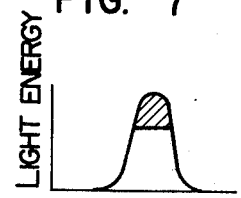
FIG. 7 is a sectional view taken along the line A—A' of FIG. 6.

As a result as shown in FIG. 5, the overall distribution $c_e$ of light energy received by the exposed area on the light sensitive film 2 is the combination of the distribution $a_e$ of light energy received when the light beam is emitted from the secondary light source 14 at the point B and the distribution $b_e$ of light energy received when the secondary light source 14 is displaced from the point A to the point C. The hatched areas shown in FIG. 5 correspond to the hatched areas shown in FIG. 6 and shown in cross section in FIG. 7. The light sensitive film 2, except for these hatched areas, is removed in the developing process so that a multiplicity of temporary dots which are elongated and spaced apart in the longitudinal direction by a relatively small distance $a''$ are formed upon the inner surface of the face-panel 1. In FIG. 5, the chain curve $d_e$ indicates the light energy distribution when the secondary light source is not displaced.

Figure 8:
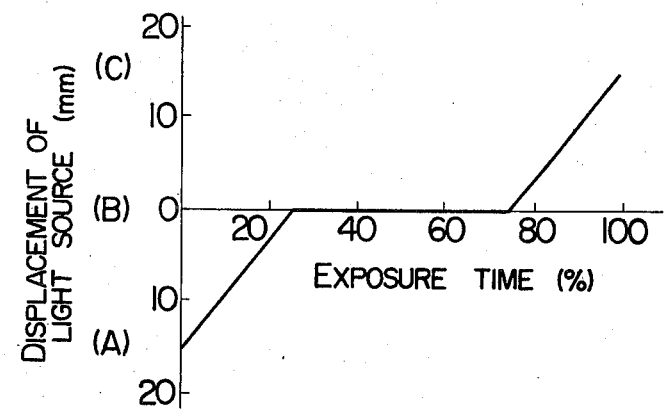
FIGS. 8, 9 and 11 are diagrams used for explanation of the mode of displacement of a secondary light source of the apparatus shown in FIG. 4.

FIG. 8 shows the relationship between the exposure time and the displacement of the secondary light source 14. It is seen that when the total exposure time is 100%, about 50% is used for the exposure at the point B while the remaining 50% is used for the displacement of the secondary light source 14 from the point A to the point B and from the point B to the point C. Since the exposure time at the point B has a considerable effect upon the spacing in the longitudinal direction between the temporary dots, it is preferable to limit the exposure time at the point B to 20 to 70%, more preferably to 40 to 55%.

Figure 9:
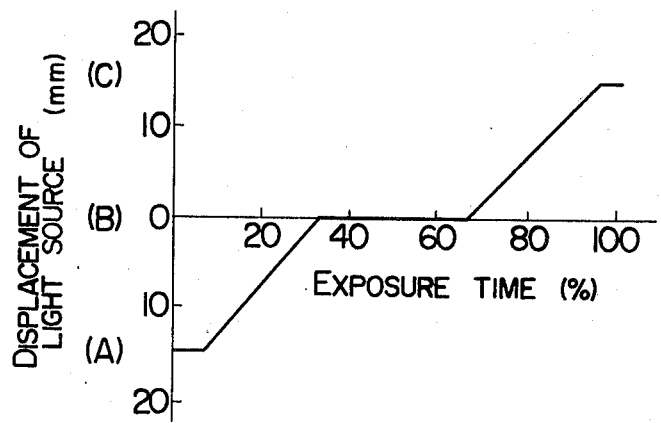
Figure 10:
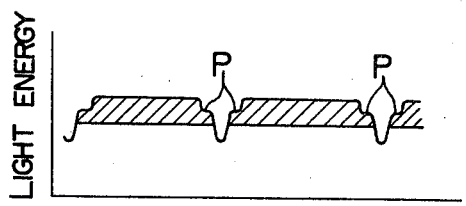
FIG. 10 is a diagram illustrating the light energy distribution in an area exposed by a second embodiment of the present invention.

According to the present invention, the secondary light source 14 may be stopped at the points A and C for a predetermined time as shown in FIG. 9, so that the spacing in the longitudinal direction between the temporary dots may be further reduced. Furthermore, the configurations at the ends of the exposed area or the temporary dot may be considerably improved because the light energy distribution with the stopped portions P may be obtained as shown in FIG. 10. Preferably, the exposure time at the point B is 20 to 50% of the overall exposure time 100% while the exposure at rest at the points A and C is 3 to 15%.

So far, the secondary light source 14 has been described as being displaced from the point A to the point C, but it may be displaced only between the points B and A or B and C. In this case, a light energy distribution pattern similar to that shown in FIG. 5 may be obtained. Furthermore, the exposure at rest at the point A or C may be also accomplished. Especially when the exposure at rest at the point A or C is made approximately 2 times as long as the exposure time at rest when the secondary light source 14 is displaced from the point A to the point B, a satisfactory end configuration and spacing in the longitudinal direction may be attained. That is, the exposure time at rest at the point B is 20 to 50% of the overall exposure time while the exposure at rest at the point A or C is 6 to 30%.

Figure 11:
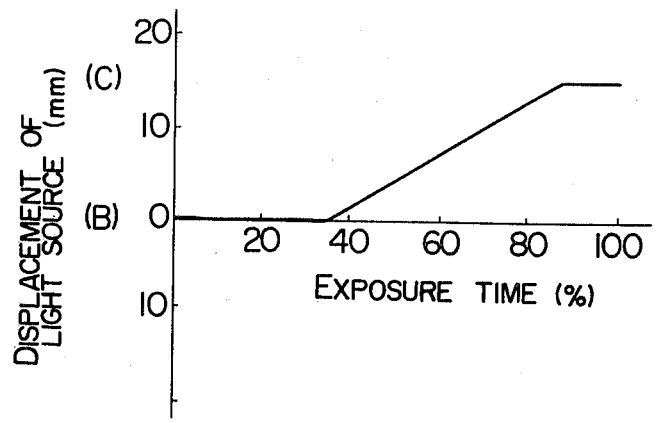

FIG. 11 is a diagram illustrating the relation between the exposure time in % and the displacement in mm of the secondary light source from the point B to C.

The rotational speed of the light source for producing the secondary light source 14 is, for instance, 50 to 200 r.p.m., and the overall exposure time in each step is of the order of about 50 to 300 seconds. The secondary light source 14 is displaced from the center point B to the point A or C by ± 5 to 30 mm.

Figure 12:
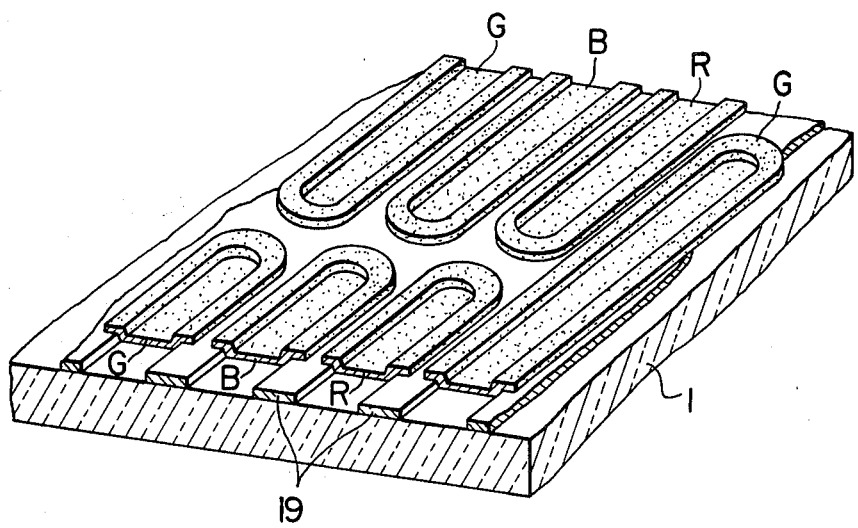
FIG. 12 is a fragmentary perspective view of the screen of a color television picture tube produced according to the present invention.

In the case of a color television picture tube with three inline electron guns, three exposure steps are cycled with the light source at three centers of deflection located on a horizontal line. Thereafter, the exposed light sensitive film is subjected to the developing process. Therefore, the temporary dots, about three times in number as the apertures in the shadow mask, may be formed upon the inner surface of the face-panel 1. A light absorbing film consisting of, for instance, graphite is uniformly coated over the inner surface of the face-panel 1, and then the temporary dots and the light absorbing film overlying thereupon are removed by any conventional manner so that the light absorbing film having a multiplicity of apertures or black matrix 19 is produced as shown in FIG. 12. Thereafter, green, blue and red phosphor color dots or strips G, B and R are deposited on the areas previously occupied by the temporary dots as shown in FIG. 12. For deposition of the color strips G, B and R, the exposure apparatus used for formation of the temporary dots is also required. However, the shape of each color strip is essentially determined by the black matrix so that strict control of the shape of the color strips is not required. Therefore, displacement of the ring-shaped secondary light source 14 may be omitted.

As described hereinbefore, according to the present invention, during the selective exposure of a light sensitive film uniformly coated upon the inner surface of a face-panel, the light emitting point of the exposure light source or secondary light source is not only rotated in a plane substantially parallel with the light sensitive film but also displaced relative to the film in the longitudinal direction of the slots in the shadow mask. Therefore, the color television picture tubes with excellent brightness and contrast characteristics may be produced without adversely affecting the mechanical strength of the shadow mask.

What is claimed is:

1. A method of manufacturing a color television picture tube having a face-panel, a light sensitive film coated over the inner surface of said face panel and a shadow mask having a plurality of slots therein spaced from said face-panel, said tube having a main axis essentially perpendicular to the surface of said face-panel and said shadow mask, wherein said method comprises the steps of:
   disposing a light source providing a light emitting point opposite said face-panel, said shadow mask being located between said face-panel and said light source, and
   rotating said light emitting point about an axis which is substantially parallel to the main axis of said tube to produce a ring-shaped secondary light source while continuously displacing said secondary light source relative to said film in the longitudinal direction of the slots in said shadow mask along a line of predetermined length from one end thereof to the other, said secondary light source being stopped at the midpoint of said line for a predetermined period of time, said light sensitive film thereby being selectively exposed to said light source.

2. A method as set forth in claim 1, wherein said secondary light source displaced continuously relative to said light sensitive film along said line of predetermined length from one end thereof to the other is stopped at said one and the other ends and at the midpoint of said line for predetermined periods of time.

3. A method as set forth in claim 2, wherein said one and the other ends are so selected that the light image projected upon said light sensitive film through one slot in said shadow mask from said secondary light source at said one or the other end may substantially register with the light image projected upon said light sensitive film through another slot in said shadow mask adjacent to said first mentioned slot in the longitudinal direction thereof from said secondary light source at said midpoint.

* * * * *